US012551335B2

(12) United States Patent
Taber et al.

(10) Patent No.: US 12,551,335 B2
(45) Date of Patent: Feb. 17, 2026

(54) HYDRAULIC DELIVERY OF SURGICAL IMPLANTS

(71) Applicant: Alcon Inc., Fribourg (CH)

(72) Inventors: Todd Taber, Keller, TX (US); Jestwin Lee, IV, Grandview, TX (US); Kathryn Jensen, Sugar Land, TX (US); Pradeep Magadum, Arlington, TX (US); Saumya Dilip Yadav, Arlington, TX (US)

( * ) Notice: Subject to any disclaimer, the term of this patent is extended or adjusted under 35 U.S.C. 154(b) by 291 days.

(21) Appl. No.: 18/350,059

(22) Filed: Jul. 11, 2023

(65) Prior Publication Data

US 2024/0016600 A1 Jan. 18, 2024

Related U.S. Application Data

(60) Provisional application No. 63/368,173, filed on Jul. 12, 2022.

(51) Int. Cl.
*A61F 2/16* (2006.01)

(52) U.S. Cl.
CPC ............ *A61F 2/1678* (2013.01); *A61F 2/167* (2013.01)

(58) Field of Classification Search
CPC ............................... A61F 2/1678; A61F 2/167
See application file for complete search history.

(56) References Cited

U.S. PATENT DOCUMENTS

| | | | |
|---|---|---|---|
| 7,156,854 | B2 | 1/2007 | Brown et al. |
| 8,308,736 | B2 | 11/2012 | Boukhny et al. |
| 8,308,799 | B2 | 11/2012 | Chen et al. |
| 8,377,076 | B2 | 2/2013 | Downer et al. |
| 8,956,408 | B2 | 2/2015 | Smiley et al. |
| 8,968,396 | B2 | 3/2015 | Matthews et al. |
| 9,480,555 | B2 | 11/2016 | Downer et al. |
| 9,610,155 | B2 | 4/2017 | Matthews et al. |
| 9,693,858 | B2 | 7/2017 | Hildebrand et al. |
| 9,855,139 | B2 | 1/2018 | Matthews et al. |
| 10,172,706 | B2 | 1/2019 | Auld et al. |
| 10,195,020 | B2 | 2/2019 | Matthews et al. |

(Continued)

FOREIGN PATENT DOCUMENTS

| | | | |
|---|---|---|---|
| EP | 1800623 | A1 | 6/2007 |
| EP | 1857076 | B1 | 7/2010 |

(Continued)

OTHER PUBLICATIONS

Written Opinion of the International Searching Authority PCT/IB2023/057106 (Oct. 24, 2023).

*Primary Examiner* — Ashley L Fishback
(74) *Attorney, Agent, or Firm* — Darin Deaver

(57) ABSTRACT

A system or apparatus for using a cartridge for eye surgery. An implant may be mechanically advanced to a sealed position in a first phase, and then the implant may be advanced into the eye via hydraulic pressure or fluid flow in a second phase. An actuator may comprise a hollow plunger and a chamber configured to receive the cartridge. The actuator may be configured to fluidly couple the cartridge to an implant bay. In a first delivery phase, the actuator may move the plunger to advance the implant into a nozzle. In a second delivery phase, the actuator may move a working fluid from the cartridge through the plunger to advance the implant through the nozzle.

18 Claims, 5 Drawing Sheets

(56) References Cited

U.S. PATENT DOCUMENTS

| | | | |
|---|---|---|---|
| 10,568,735 B2 | 2/2020 | Brown et al. | |
| 10,588,780 B2 | 3/2020 | Van Noy et al. | |
| 11,039,953 B2 | 6/2021 | Balachandran | |
| 12,004,944 B2 | 6/2024 | Weston | |
| 2008/0097460 A1 | 4/2008 | Boukhny et al. | |
| 2008/0147081 A1 | 6/2008 | Pynson | |
| 2008/0221584 A1 | 9/2008 | Downer | |
| 2010/0057093 A1 | 3/2010 | Ide et al. | |
| 2011/0265779 A1 | 11/2011 | Vandrak et al. | |
| 2012/0022548 A1 | 1/2012 | Zacharias | |
| 2013/0197532 A1 | 8/2013 | Boukhny et al. | |
| 2013/0253527 A1 | 9/2013 | Schneider et al. | |
| 2014/0012277 A1 | 1/2014 | Matthews et al. | |
| 2014/0257315 A1* | 9/2014 | Wu | A61F 2/1672 606/107 |
| 2014/0276898 A1 | 9/2014 | Novak et al. | |
| 2015/0238687 A1 | 8/2015 | Novakovic et al. | |
| 2015/0282928 A1 | 10/2015 | Auld et al. | |
| 2016/0087460 A1 | 3/2016 | Rich et al. | |
| 2017/0007237 A1 | 1/2017 | Yates et al. | |
| 2017/0027686 A1 | 2/2017 | Nagasaka et al. | |
| 2017/0119522 A1 | 5/2017 | Auld et al. | |
| 2018/0049866 A1 | 2/2018 | Fayyaz et al. | |
| 2018/0200046 A1 | 7/2018 | Brown et al. | |
| 2018/0200047 A1 | 7/2018 | Wu et al. | |
| 2020/0179101 A1 | 6/2020 | Flowers et al. | |
| 2020/0179102 A1 | 6/2020 | Chen et al. | |
| 2020/0179103 A1 | 6/2020 | Auld et al. | |
| 2020/0188089 A1 | 6/2020 | Auld et al. | |
| 2020/0197170 A1 | 6/2020 | Auld et al. | |
| 2021/0052371 A1 | 2/2021 | Singh et al. | |
| 2021/0369446 A1 | 12/2021 | Taber et al. | |
| 2022/0142767 A1 | 5/2022 | Taber et al. | |
| 2022/0175517 A1 | 6/2022 | Lee, IV et al. | |
| 2022/0192819 A1* | 6/2022 | Rodeheaver | A61F 2/1678 |
| 2022/0265420 A1 | 8/2022 | Kelp | |

FOREIGN PATENT DOCUMENTS

| | | | |
|---|---|---|---|
| EP | 3560457 | A1 | 10/2019 |
| JP | 2010063777 | B | 10/2013 |
| JP | 2016503716 | A | 2/2016 |
| WO | 2014145562 | A1 | 9/2014 |
| WO | 2020065516 | A1 | 4/2020 |
| WO | 2020128762 | A1 | 6/2020 |
| WO | 2020151908 | A1 | 7/2020 |
| WO | 2021154203 | A1 | 8/2021 |
| WO | 2022101690 | A1 | 5/2022 |
| WO | 2022118249 | A1 | 6/2022 |

* cited by examiner

HYDRAULIC DELIVERY OF SURGICAL IMPLANTS

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims Illustrative embodiments are also provided to enable a person skilled in the art to make and use the claimed subject matter.

For example, some embodiments may comprise or consist essentially of an apparatus for delivering an implant, such as an intraocular lens, using hydraulic pressure or fluid flow. The apparatus may be combined with a disposable hydraulic cartridge, such as a vial of working fluid, to provide a fully disposable system for storing, advancing, and delivering an implant.

In more particular examples, the apparatus may comprise a rigid plunger for advancing an implant to a sealed position in a first phase, and a bore through the rigid plunger that allows a working fluid to advance the implant into the eye via hydraulic pressure in a second phase. For example, a hollow rigid plunger can be used to first advance an intraocular lens with haptics in a straightented configuration to a point that a seal is created about the intraocular lens within a delivery lumen. The lens may then be hydraulically advanced to delivery by passing a working fluid through the hollow bore of the plunger. The apparatus may additionally comprise a plunger stop, which may be configured to stop advancement of the implant interface or the plunger.

In yet more particular embodiments, the apparatus may have a nozzle, a plunger, a plunger rod, and a chamber configured to receive a cartridge between the plunger and the plunger rod. To maintain a compact configuration, the plunger rod may be placed in a forward position for shipping and storage. For operation, the plunger rod may be placed in an aft position to allow the cartridge to be inserted into the chamber between the plunger and the plunger rod. The plunger rod may be advanced toward the cartridge to couple the cartridge to the plunger. The plunger rod, the cartridge, and the plunger may be advanced further to advance the implant to a sealed position in the nozzle. Further advancement of the plunger rod can drive a working fluid from the cartridge and through a bore in the plunger to eject the implant from the nozzle.

More generally, a system for using a cartridge for eye surgery may comprise a nozzle, an implant bay coupled to the nozzle, an implant disposed in the implant bay, and an actuator. The actuator may comprise a plunger and a chamber configured to receive the cartridge. The actuator may be configured to fluidly couple the cartridge to the implant bay. In a first delivery phase, the actuator may move the plunger to advance the implant into the nozzle. In a second delivery phase, the actuator may move a working fluid from the cartridge through the plunger to advance the implant through the nozzle. In more particular embodiments, the actuator may further comprise a plunger rod and a bore through the plunger. The plunger rod may be configured to advance the plunger and to move the working fluid from the cartridge through the bore to advance the implant through the nozzle. Some embodiments of the plunger may comprise a coupling configured to fluidly couple the cartridge to the implant bay. Additionally, or alternatively, some embodiments of the system may comprise a lead nut, which may be threaded onto a threaded portion of the plunger rod. The plunger rod may be configured to be rotated through the lead nut to move the working fluid and may be configured to maintain a relative position between the plunger rod and the cartridge as the implant is advanced from the implant bay to the nozzle. In yet more particular embodiments, the cartridge may comprise a cartridge seal, and the plunger rod may be configured to advance the cartridge seal to move the working fluid. For example, the plunger rod may be configured to be rotated through a lead nut to advance the cartridge seal.

In other examples, a system for using a hydraulic cartridge for eye surgery may comprise a nozzle, an implant bay coupled to the nozzle, an implant disposed in the implant bay, a housing coupled to the implant bay, a plunger disposed within the housing, and a plunger rod at least partially disposed within the housing. The system may additionally comprise a bore through the plunger, which can be fluidly coupled to the implant bay. A chamber may be configured to receive the hydraulic cartridge between the plunger and the plunger rod. The plunger rod may be configured to move the hydraulic cartridge and the plunger within the housing to advance the implant from the implant bay to the nozzle in a first delivery phase. The plunger rod may be operable to drive a working fluid from the hydraulic cartridge through the bore to advance the implant through the nozzle in a second delivery phase.

In yet other examples, a system for using a hydraulic cartridge for eye surgery may comprise a nozzle, an implant bay coupled to the nozzle, an implant disposed in the implant bay, a housing coupled to the implant bay, a plunger configured to slide within the housing, a bore through the plunger, and a plunger rod having a threaded end disposed within the housing. A lead nut may be threaded onto the threaded end of the plunger rod, and a chamber may be configured to receive the hydraulic cartridge between the plunger and the lead nut. The plunger rod may be configured to be pushed or to otherwise slide to advance the lead nut, the hydraulic cartridge, and the plunger to advance the implant from the implant bay to the nozzle in a first delivery phase. The plunger rod may be configured to be rotated through the lead nut to drive a working fluid from the hydraulic cartridge through the bore to advance the implant through the nozzle in a second delivery phase.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
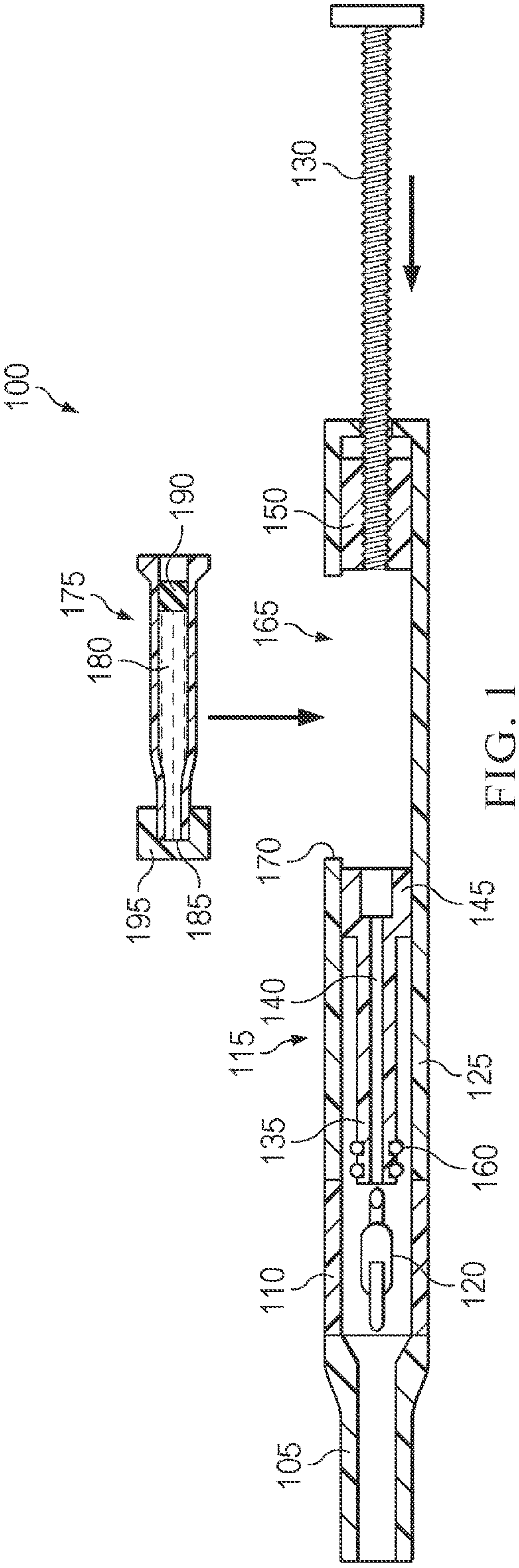
FIG. 1 is a schematic diagram of an example system for delivering an implant into an eye.

FIG. 1 is a schematic diagram of a system 100 that can be used to deliver an implant into an eye. For example, as illustrated in FIG. 1, some embodiments of the system 100 may include a nozzle 105, an implant bay 110 that can be coupled to the nozzle 105, and an actuator 115 that can be coupled to the implant bay 110. Initially, various components of the system 100 may be assembled if needed. In the example of FIG. 1, the nozzle 105, the implant bay 110, and the actuator 115 are fixed together to form a unitary structure. In other embodiments, the system 100 may comprise two or more modules, which can be configured to be coupled and decoupled as appropriate for storage, assembly, use, and disposal.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically and fluidly coupled to the nozzle 105. In some embodiments, components may also be coupled by virtue of physical proximity, being integral to a single structure, or being formed from the same piece of material.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In FIG. 1, for example, an implant 120 is disposed within the implant bay 110. In some embodiments, the implant 120 may comprise an intraocular lens having a shape similar to that of a natural lens of an eye, and it may be made from numerous materials. Examples of suitable materials may include silicone, acrylic, and combinations of such suitable materials. In some instances, the implant 120 may comprise an intraocular lens that is fluid-filled, such as a fluid-filled accommodating intraocular lens. The implant 120 may also comprise an intraocular lens that includes one or more features for positioning the intraocular lens within an eye. For example, the implant 120 may comprise one or more haptics, which can be oriented by the implant bay 110 prior to delivery.

In some embodiments, the implant bay 110 may additionally or alternatively be configured to prepare the implant 120 for delivery. For example, some embodiments of the implant bay 110 may be configured to be actuated by a surgeon or other operator to prepare the implant 120 for delivery by subsequent action of the actuator 115. In some instances, the implant bay 110 may be configured to actively deform, elongate, extend, or otherwise manipulate features of the implant 120 before the implant 120 is advanced into the nozzle 105. For example, some embodiments of the implant bay 110 may be configured to orient, fold, or splay an implant.

The actuator 115 of FIG. 1 generally comprises a housing 125, a plunger rod 130, a plunger 135, and a bore 140 through the plunger 135. The plunger rod 130 and the plunger 135 are generally comprised of a substantially rigid material, such as a medical grade polymer material. The plunger 135 may additionally comprise a coupling 145. A lead nut 150 may be coupled to the plunger rod 130. A portion of the plunger 135 may extend into the implant bay 110.

In some embodiments, the actuator 115 may additionally comprise a nozzle seal 160. As illustrated in the example of FIG. 1, the nozzle seal 160 may be a ring seal, such as an O-ring, disposed circumferentially around a portion of the plunger 135. In other examples, an umbrella seal may be suitable. In more particular embodiments, the nozzle seal 160 may be disposed distal to the coupling 145.

As illustrated in the example of FIG. 1, the system 100 may also comprise a chamber 165. The chamber 165 of FIG. 1 is generally formed between the plunger 135 and an end of the housing 125 and may be accessible through a slot 170 in the housing 125 or other suitable opening in the actuator 115. In some configurations, the plunger rod 130 may be advanced toward the plunger 135 to reduce the length of the system 100, which may be advantageous for transporting and storing the system 100. Before use, the plunger rod 130 may be retracted to open the chamber 165, as illustrated in the example of FIG. 1.

The chamber 165 may be configured to receive a cartridge 175, which may contain a working fluid 180. Suitable working fluids may include, without limitation, a liquid, such as saline, or a viscous lubricant with non-Newtonian properties. The cartridge 175 may then be inserted into the chamber 165 to prepare the system 100 to deliver the implant 120. In other examples, the cartridge 175 may be transported and stored in the chamber 165. The cartridge 175 generally comprises a cartridge tip 185 and a cartridge seal 190. A cap 195 may be initially disposed over the cartridge tip 185. The cartridge seal 190 and the cap 195 together may contain the working fluid 180 within the cartridge 175, which may be suitable for transporting and storing the cartridge 175. In some embodiments, the cartridge 175 may comprise or consist essentially of a vial of working fluid. Suitable working fluids may include, without limitation, a liquid, such as saline, or a viscous lubricant with non-Newtonian properties.

Figure 2A:
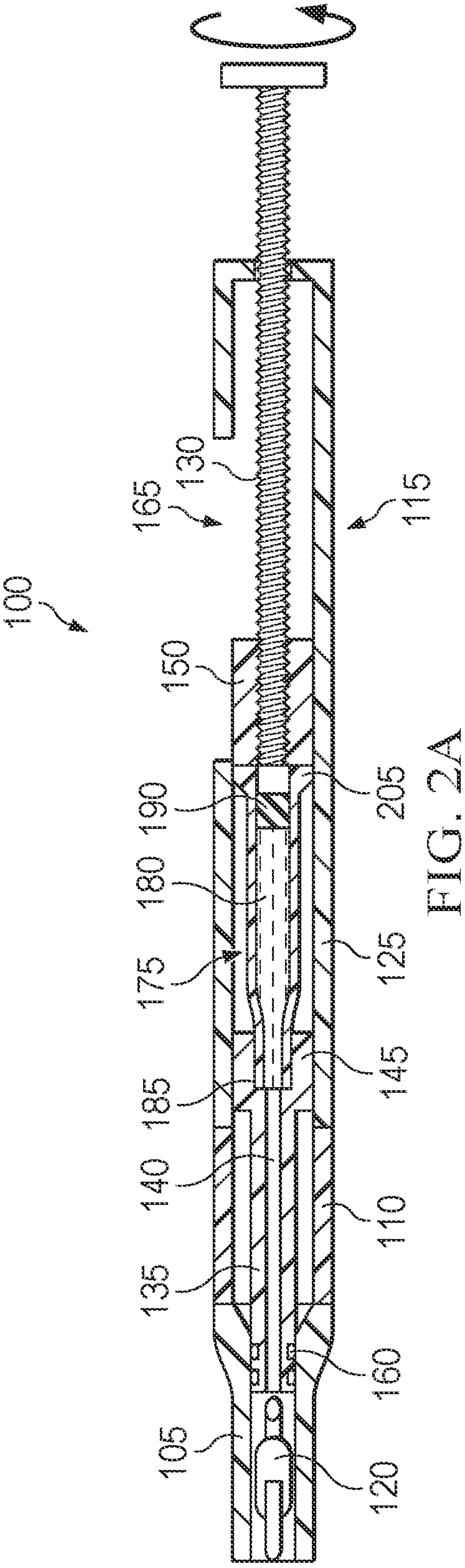
FIG. 2A and FIG. 2B are schematic diagrams illustrating an example operation of the system of FIG. 1.
Figure 2B:
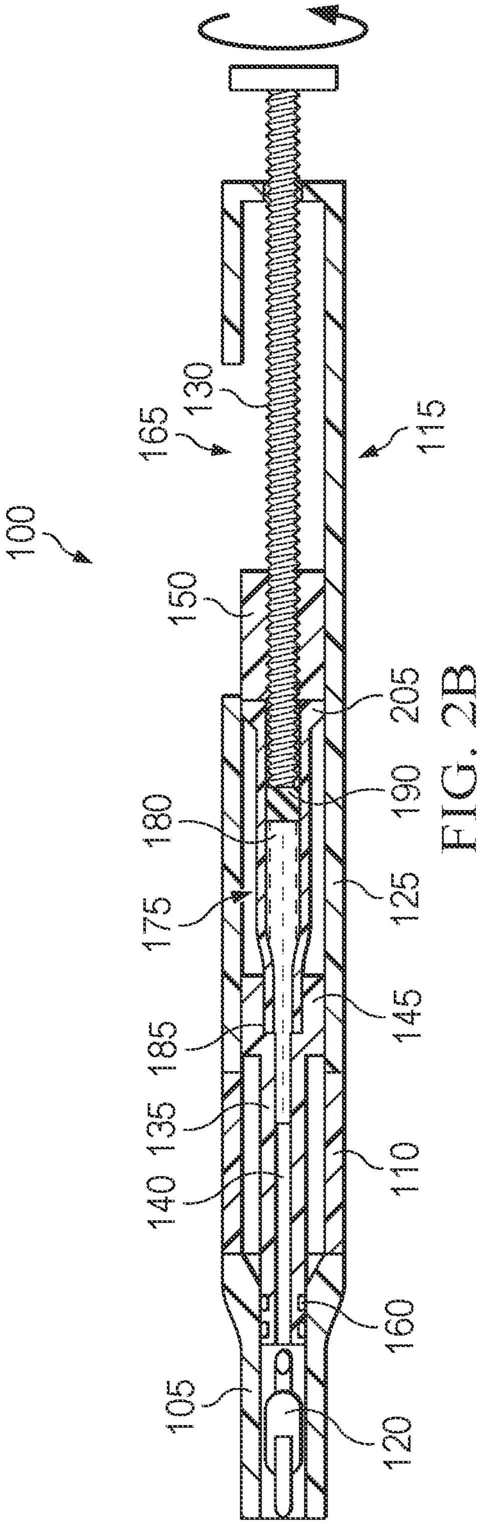

FIG. 2A and FIG. 2B are also schematic diagrams of the system 100, illustrating additional details that may be associated with the use of some embodiments. The actuator 115 is generally configured to allow the plunger 135 to advance the implant 120 mechanically from the implant bay 110 into the nozzle 105 in a first phase of delivery, as illustrated in the example of FIG. 2A, and to allow the working fluid 180 to be moved from the cartridge 175 through the implant bay 110 and the nozzle 105 to advance the implant 120 fluidly or hydraulically through the nozzle 105 in a second phase, as illustrated in the example of FIG. 2B.

For example, if assembled as illustrated in FIG. 2A and FIG. 2B, the implant bay 110 may be disposed between the nozzle 105 and the actuator 115. In the example of FIG. 2A and FIG. 2B, the cap 195 (not shown) has been removed from the cartridge tip 185, and the cartridge 175 has been inserted into the chamber 165. The actuator 115 may fluidly couple the working fluid 180 in the cartridge 175 to the implant bay 110 and/or the nozzle 105. For example, the coupling 145 may be configured to receive the cartridge tip 185 and to fluidly couple the working fluid 180 in the cartridge 175 to the implant bay 110 and the nozzle 105 through the bore 140, as illustrated in FIG. 2A and FIG. 2B. The plunger rod 130 may also be coupled to the cartridge 175. For example, the plunger rod 130, or a portion thereof, may be configured to slide within the housing 125 to push the cartridge 175, which in turn can push the plunger 135 and the implant 120 in the first delivery phase. In more particular examples, the lead nut 150 may engage the cartridge 175 opposite the cartridge tip 185 to advance the cartridge 175 through the chamber 165 as the plunger rod 130 is advanced.

In the example of FIG. 2A, the cartridge 175 has been inserted into the chamber 165, and the plunger rod 130 has been pushed to advance the cartridge 175 and the plunger 135. As illustrated in FIG. 2A, the lead nut 150 can maintain a relative position of the plunger rod 130 and the cartridge 175 as both advance through the housing 125 in the first delivery phase. For example, some embodiments of the plunger rod 130 may have a threaded end disposed within the housing 125, and the lead nut 150 may be threaded onto the threaded end of the plunger rod 130. If the plunger rod 130 is pushed, the lead nut 150 may apply force to a flange 205 of the cartridge 175 to rigidly move the cartridge 175 and the plunger 135 while maintaining the relative position of the plunger rod 130 and the cartridge seal 190, thereby allowing the working fluid 180 to be retained in the cartridge 175.

In the example of FIG. 2A, the implant 120 has also been advanced into the nozzle 105 by plunger 135. The nozzle seal 160 has also been advanced into the nozzle 105 to create a seal in the nozzle 105 behind the implant 120. In some examples, the nozzle seal 160 may also prevent further advancement of the plunger 135 and the cartridge 175. In other examples, the system 100 may have a plunger stop configured to prevent further advancement. The implant 120 may also form a seal within the nozzle 105 in some instances. In the configuration of FIG. 2A, the bore 140 may fluidly couple the working fluid 180 in the cartridge 175 to the nozzle 105.

As illustrated in the example of FIG. 2B, with the implant 120 advanced into the nozzle 105, the plunger rod 130 may be advanced from the position of FIG. 2A to move the working fluid 180 from the cartridge 175 through the plunger 135 in a second phase of delivery. For example, the plunger rod 130 may be twisted to advance a distal end of the plunger rod 130 through threads in the lead nut 150, while the housing 125 can prevent rotation of the lead nut 150. Advancing the plunger rod 130 can advance the cartridge seal 190, which can force the working fluid 180 through the bore 140 into the nozzle 105 behind the implant 120. Movement of the working fluid 180 from the bore 140 into the nozzle 105 under pressure from the cartridge seal 190 can increase the pressure and flow rate of the working fluid 180 in the nozzle 105 behind the implant 120, which can advance the implant 120 further through the nozzle 105 until the implant 120 is ejected from the nozzle 105.

Figure 3:
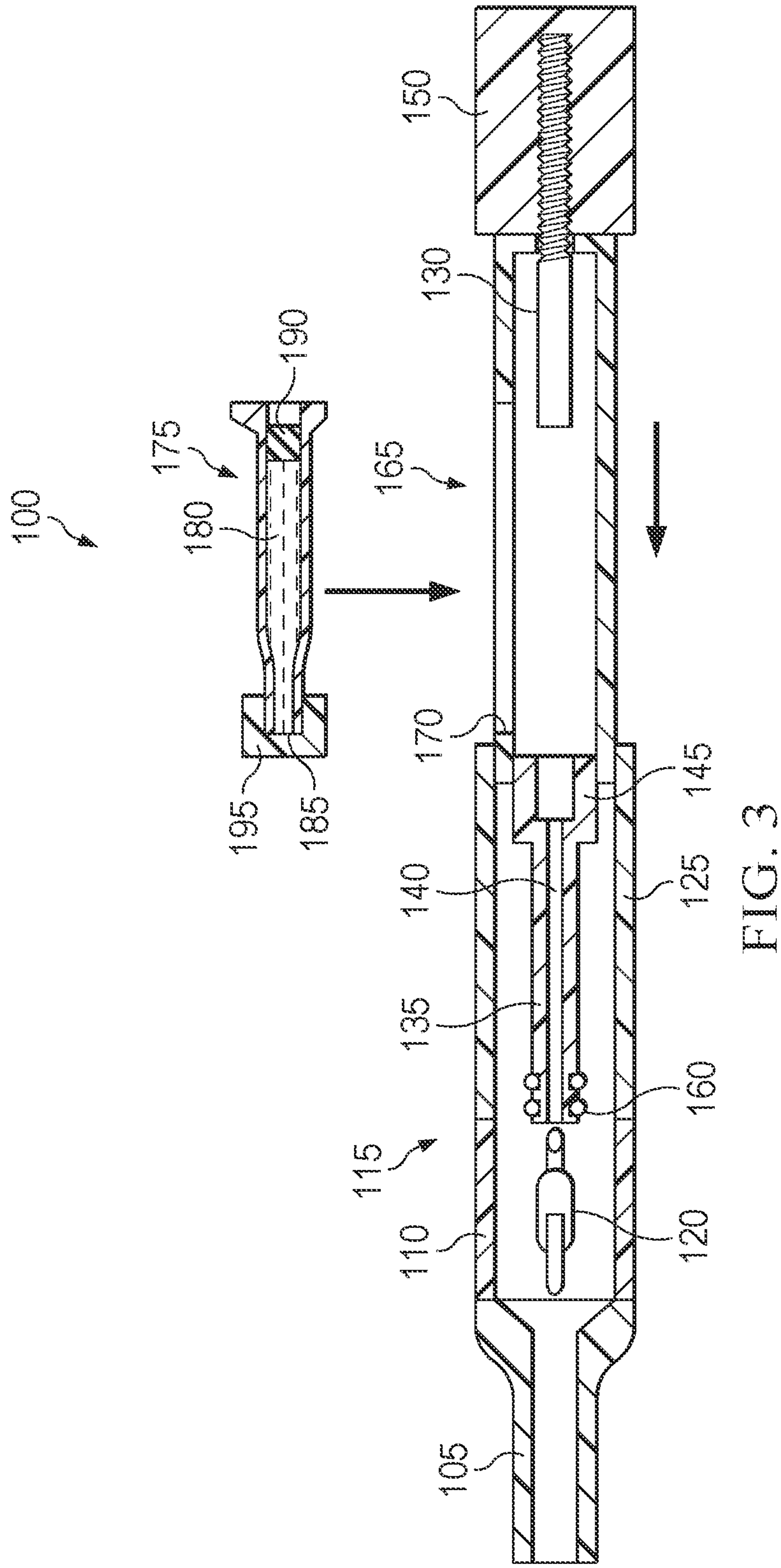
FIG. 3 is a schematic diagram of another example system for delivering an implant into an eye.

FIG. 3 is a schematic diagram of another example of the system 100, which can be used to deliver an implant into an eye. The example of FIG. 3 is similar or analogous to the example of FIG. 1 in several respects. For example, the system 100 of FIG. 3 may include the nozzle 105, the implant bay 110, and the actuator 115.

The actuator 115 of FIG. 3 generally comprises the housing 125, the plunger rod 130, the plunger 135, and the bore 140 through the plunger 135. The plunger 135 may additionally comprise the coupling 145. In the example of FIG. 3, the lead nut 150 may be coupled to a threaded portion of the plunger rod 130 and coupled to an end of the housing 125. In more particular examples, a threaded portion of the plunger rod may extend through a wall in the chamber 165, and the lead nut 150 may be coupled to the chamber 165. A portion of the plunger 135 may extend into the implant bay 110.

The chamber 165 of FIG. 3 is generally formed between the plunger 135 and the lead nut 150 and may be accessible through the slot 170 or other suitable opening in the actuator 115. In some configurations, the chamber 165 may be advanced toward the plunger 135 to reduce the length of the system 100, which may be advantageous for transporting and storing the system 100. In FIG. 3, for example, a portion of the chamber 165 may slide over at least a portion of the plunger 135, between the housing 125 and the plunger 135. Before use, the chamber 165 may be retracted to expose the slot 170, as illustrated in the example of FIG. 3.

Figure 4A:
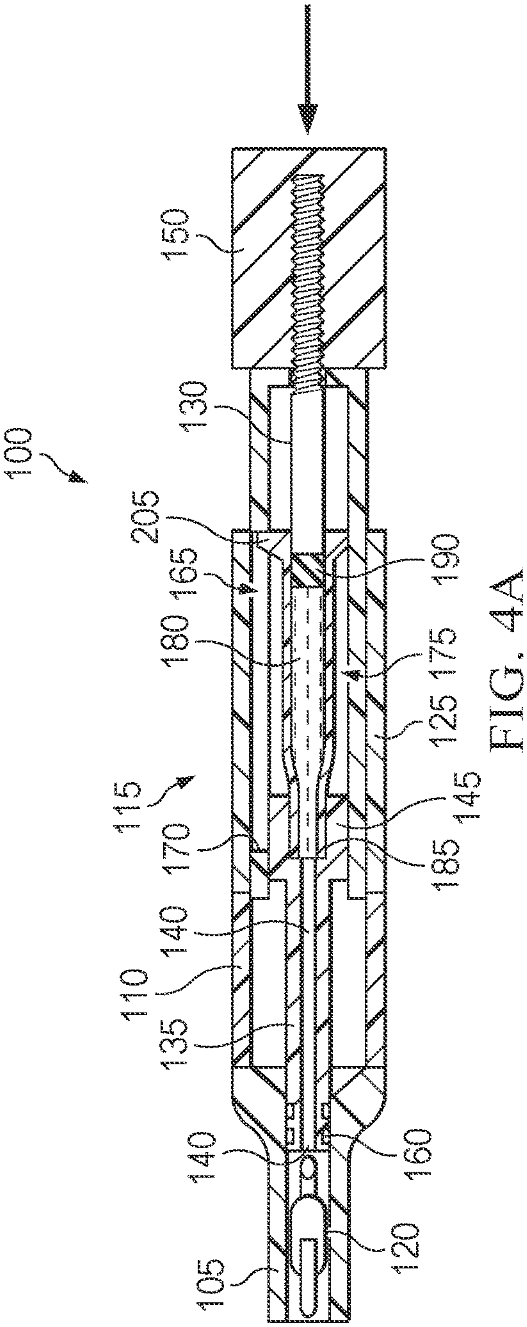
FIG. 4A and FIG. 4B are schematic diagrams illustrating an example operation of the system of FIG. 3.
Figure 4B:
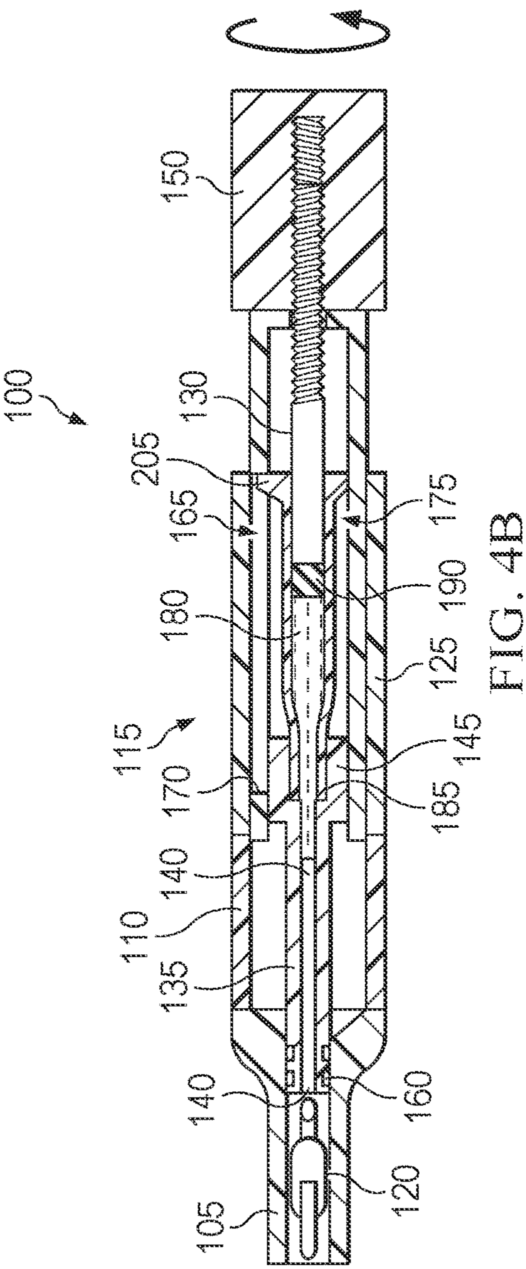

FIG. 4A and FIG. 4B are also schematic diagrams of the system 100 of FIG. 3, illustrating additional details that may be associated with the use of some embodiments. The actuator 115 is generally configured to allow the plunger 135 to advance the implant 120 mechanically from the implant bay 110 into the nozzle 105 in a first phase of delivery, as illustrated in the example of FIG. 4A, and to allow the working fluid 180 to be moved from the cartridge 175 through the implant bay 110 and the nozzle 105 to advance the implant 120 fluidly or hydraulically through the nozzle 105 in a second phase, as illustrated in the example of FIG. 4B.

For example, if assembled as illustrated in FIG. 4A and FIG. 4B, the implant bay 110 may be disposed between the nozzle 105 and the actuator 115. In the example of FIG. 4A and FIG. 4B, the cap 195 (not shown) has been removed from the cartridge tip 185, and the cartridge 175 has been inserted into the chamber 165. The actuator 115 may fluidly couple the working fluid 180 in the cartridge 175 to the implant bay 110 and/or the nozzle 105. For example, the coupling 145 may be configured to receive the cartridge tip 185 and to fluidly couple the working fluid 180 in the cartridge 175 to the implant bay 110 and the nozzle 105 through the bore 140, as illustrated in FIG. 4A and FIG. 4B. The plunger rod 135 may be coupled to cartridge seal 190. The chamber 165, or a portion thereof, may be configured to slide within the housing 125 to push the cartridge 175, which in turn can push the plunger 135 and the implant 120 in the first delivery phase. In more particular examples, the slot 170 may engage the cartridge 175 opposite the cartridge tip 185.

In the example of FIG. 4A, the cartridge 175 has been inserted into the chamber 165, and the chamber 165 has been pushed to advance the cartridge 175 and the plunger 135. As illustrated in FIG. 4A, the lead nut 150 can maintain a relative position of the plunger rod 130 and the cartridge 175 as both advance through the housing 125 in the first delivery phase. For example, some embodiments of the plunger rod 130 may have a threaded end disposed within the lead nut 150, and the lead nut 150 may be coupled to an end of the chamber 165. If the lead nut 150 is pushed, the slot 170 may apply force to the flange 205 of the cartridge 175 to rigidly move the cartridge 175 and the plunger 135 while maintaining the relative position of the plunger rod 130 and the cartridge seal 190, thereby allowing the working fluid 180 to be retained in the cartridge 175.

In the example of FIG. 4A, the implant 120 has also been advanced into the nozzle 105 by plunger 135. The nozzle seal 160 may also be advanced into the nozzle 105 to create a seal in the nozzle 105 behind the implant 120. In some examples, the nozzle seal 160 may also prevent further advancement of the plunger 135 and the cartridge 175. In other examples, the system 100 may have a plunger stop configured to prevent further advancement. The implant 120 may also form a seal within the nozzle 105 in some instances. In the configuration of FIG. 4A, the bore 140 may fluidly couple the working fluid 180 in the cartridge 175 to the nozzle 105.

As illustrated in the example of FIG. 4B, with the implant 120 advanced into the nozzle 105, the plunger rod 130 may be advanced from the position of FIG. 4A to move the working fluid 180 from the cartridge 175 through the plunger 135 in a second phase of delivery. For example, the lead nut 150 may be twisted to advance the plunger rod 130 through threads in the lead nut 150, while the chamber 165 can prevent rotation of the plunger rod 130. Advancing the plunger rod 130 can advance the cartridge seal 190, which can force the working fluid 180 through the bore 140 into the nozzle 105 behind the implant 120. Movement of the working fluid 180 from the bore 140 into the nozzle 105 under pressure from the cartridge seal 190 can increase the pressure and flow rate of the working fluid 180 in the nozzle 105 behind the implant 120, which can advance the implant 120 further through the nozzle 105 until the implant 120 is ejected from the nozzle 105.

Figure 5A:
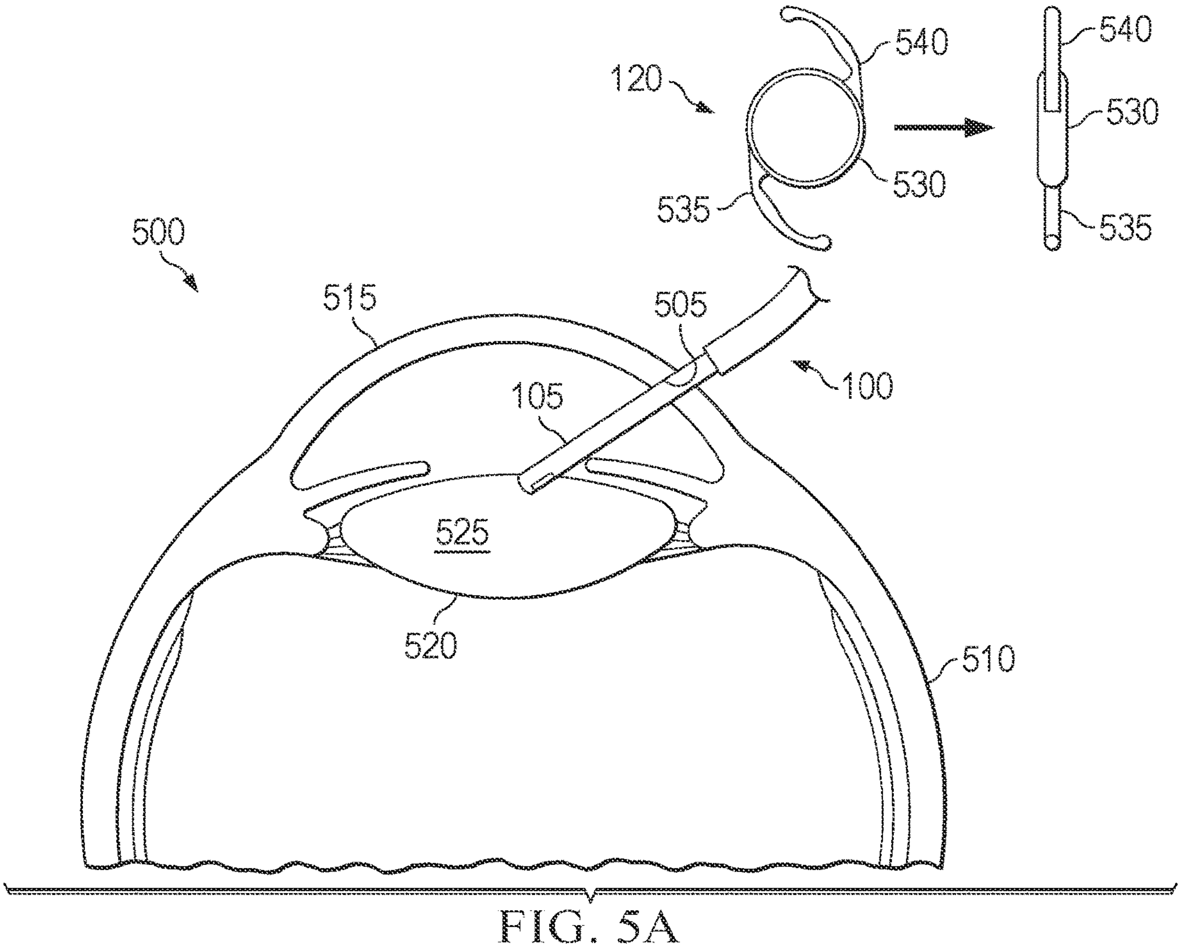
FIG. 5A and FIG. 5B are schematic diagrams further illustrating an example use of the system of FIG. 1 or FIG. 3 to deliver an implant to an eye.
Figure 5B:
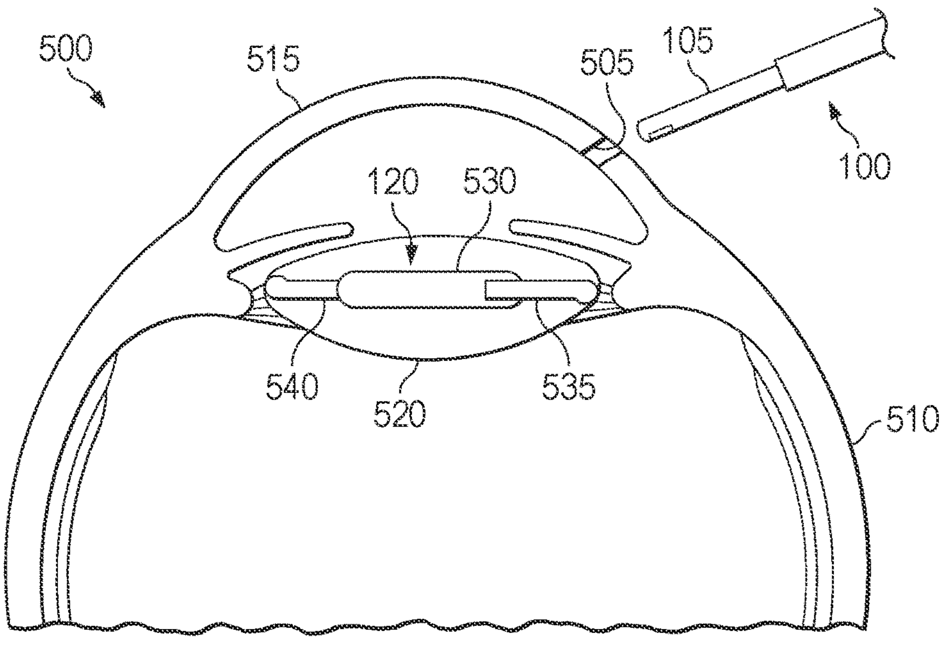

FIGS. 5A-5B are schematic diagrams further illustrating an example use of the system 100 to deliver the implant 120 to an eye 500. As illustrated, an incision 505 may be made in the eye 500 by a surgeon, for example. In some instances, the incision 505 may be made through the sclera 510 of the eye 500. In other instances, an incision may be formed in the cornea 515 of the eye 500. The incision 505 may be sized to permit insertion of a portion of the nozzle 105 to deliver the implant 120 into the capsular bag 520. For example, in some instances, the size of the incision 505 may have a length less than about 3000 microns (3 millimeters). In other instances, the incision 505 may have a length of from about 1000 microns to about 1500 microns, from about 1500 microns to about 2000 microns, from about 2000 microns to about 2500 microns, or from about 2500 microns to about 3000 microns.

After the incision 505 is made, the nozzle 105 can be inserted through the incision 505 so that the tip of the nozzle 105 aligns with the incision 505, allowing the nozzle 105 to extend into an interior portion 525 of the eye 500. The system 100 can then eject the implant 120 through the nozzle 105 into the capsular bag 520 of the eye 500, substantially as described above with reference to FIGS. 2A-2B or FIGS. 4A-4B.

In some embodiments, the implant 120 may comprise an intraocular lens. In some instances, the implant 120 may comprise an intraocular lens that is fluid-filled, such as a fluid-filled accommodating intraocular lens. The implant 120 may also comprise an intraocular lens that includes one or more features, such as haptics, for positioning the intraocular lens within an eye. In the example of FIG. 5A and FIG. 5B, the implant 120 is illustrative of an intraocular lens having an optic body 530, a leading haptic 535, and a trailing haptic 540.

In some applications, the implant 120 may be delivered in a folded, straightened, or splayed configuration and can revert to an initial, resting state, within the capsular bag 520, as shown in FIG. 5B. The capsular bag 520 can retain the implant 120 within the eye 500 in a relationship relative to the eye 500 so that the optic body 530 refracts light directed to the retina (not shown). The leading haptic 535 and the trailing haptic 540 can engage the capsular bag 520 to secure the implant 120 therein. After dispensing the implant 120 into the capsular bag 520, the nozzle 105 may be removed from the eye 500 through the incision 505, and the eye 500 can be allowed to heal over time.

The systems, apparatuses, and methods described herein may provide significant advantages. For example, some embodiments may be particularly advantageous for delivering intraocular lenses, including fluid-filled accommodating lenses, which can present unique challenges for delivery. Some embodiments can compress a relatively large lens to fit through an acceptably small incision, manage deformation caused by shifting fluid during compression and exit from a nozzle, and execute delivery in a predictable and controlled manner Additionally, some embodiments can reduce system complexity and the number of delivery steps while maintaining haptic position consistency. Some embodiments may also reduce the amount of working fluid for delivery. For example, a single vial of ophthalmic viscosurgical device (OVD), such as vial of CELLUGEL OVD, PROVISC OVD, OR DISCOVISC OVD, may be used to drive some embodiments of the system 100 and provide the working fluid for delivery. Additionally, or alternatively, some embodiments may be particularly advantageous for providing multiple delivery modes in a single apparatus. For example, a first delivery mode can allow an operator to advance an implant to a dwell position by pushing a plunger rod. A second delivery mode can allow an operator to twist the plunger rod to advance an implant, which can give the operator finer position control as the implant is delivered.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles “a” or “an” do not limit the subject to a single instance unless clearly required by the context. Components may also be combined or eliminated in various configurations for purposes of sale, manufacture, assembly, or use. For example, in some configurations, the nozzle 105, the implant bay 110, and the actuator 115 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for using a cartridge for eye surgery, the system comprising:

a nozzle;

an implant bay coupled to the nozzle; and an actuator comprising a plunger and a chamber configured to receive the cartridge;

wherein the actuator is configured to move the plunger to advance an implant from the implant bay into the nozzle, to fluidly couple a working fluid in the cartridge to the implant bay, and to move the working fluid from the cartridge through the plunger to advance the implant through the nozzle.

2. The system of claim 1, wherein the plunger comprises a coupling configured to fluidly couple the cartridge to the implant bay.

3. The system of claim 1, wherein:

the actuator further comprises a plunger rod, and a bore through the plunger; and the plunger rod is configured to move the working fluid from the cartridge through the bore to advance the implant through the nozzle.

4. The system of claim 3, further comprising a lead nut threaded onto the plunger rod, wherein the lead nut is configured to advance the plunger rod to move the working fluid.

5. The system of claim 4, wherein the lead nut is configured to maintain a relative position of the plunger rod and the cartridge as the implant is advanced from the implant bay to the nozzle.

6. The system of claim 4, wherein:

the cartridge comprises a cartridge seal; and the plunger rod is configured to advance the cartridge seal to move the working fluid.

7. The system of claim 6, wherein:

the lead nut is configured to advance the cartridge through the chamber; and the plunger rod is configured to be rotated through the lead nut to advance the cartridge seal.

8. The system of claim 6, wherein:

the chamber is configured to advance the cartridge and the plunger;

the lead nut is coupled to an end of the chamber; and the lead nut is configured to be rotated around the plunger rod to advance the cartridge seal.

9. A system for using a hydraulic cartridge for eye surgery, the system comprising:

a nozzle;

an implant bay coupled to the nozzle;

an implant disposed in the implant bay;

a housing coupled to the implant bay;

a plunger disposed within the housing;

a bore through the plunger, the bore fluidly coupled to the implant bay;

a plunger rod at least partially disposed within the housing; and a chamber configured to receive the hydraulic cartridge between the plunger and the plunger rod;

wherein the plunger is configured to advance the implant from the implant bay to the nozzle in a first delivery phase, and the plunger rod is operable to drive a working fluid from the hydraulic cartridge through the bore to advance the implant through the nozzle in a second delivery phase.

10. The system of claim 9, wherein the plunger comprises a coupling configured to receive the hydraulic cartridge and to fluidly couple the hydraulic cartridge to the bore.

11. The system of claim 9, further comprising a lead nut threaded onto the plunger rod, wherein the lead nut is configured to advance the plunger rod to drive the working fluid through the bore.

12. The system of claim 11, wherein the lead nut is configured to maintain a relative position of the plunger rod and the hydraulic cartridge as the implant is advanced from the implant bay to the nozzle.

13. The system of claim 11, wherein:

the hydraulic cartridge comprises a cartridge seal; and the plunger rod is configured to be rotated through the lead nut to advance the cartridge seal to drive the working fluid.

14. The system of claim 13, wherein:

the chamber is configured to advance the hydraulic cartridge and the plunger;

the lead nut is coupled to an end of the chamber; and the lead nut is configured to be rotated around the plunger rod to advance the cartridge seal.

15. A system for using a hydraulic cartridge for eye surgery, the system comprising:

a nozzle;

an implant bay coupled to the nozzle;

an implant disposed in the implant bay;

a housing coupled to the implant bay;

a plunger configured to slide within the housing;

a bore through the plunger, the bore fluidly coupled to the implant bay;

a plunger rod having a threaded end disposed within the housing;

a lead nut threaded onto the threaded end of the plunger rod; and a chamber configured to receive the hydraulic cartridge between the plunger and the lead nut;

wherein the plunger rod is configured to be pushed to rigidly move the lead nut, the hydraulic cartridge, and the plunger to advance the implant from the implant bay to the nozzle, and the plunger rod is configured to be rotated through the lead nut to drive a working fluid from the hydraulic cartridge through the bore to advance the implant through the nozzle.

16. The system of claim 15, wherein the plunger comprises a coupling configured to receive the hydraulic cartridge and to fluidly couple the hydraulic cartridge to the bore.

17. The system of claim 15, wherein the lead nut is configured to maintain a relative position of the plunger rod and the hydraulic cartridge as the implant is advanced from the implant bay to the nozzle.

18. The system of claim 15, wherein:

the hydraulic cartridge comprises a cartridge seal; and the plunger rod is configured to advance the cartridge seal to drive the working fluid from the hydraulic cartridge through the bore.

* * * * *